United States Patent
Howitz et al.

(10) Patent No.: US 7,278,210 B2
(45) Date of Patent: Oct. 9, 2007

(54) METHOD FOR PRODUCING A 3-D MICROSCOPE FLOW-THROUGH CELL

(75) Inventors: Steffen Howitz, Dresden (DE); Mario Buerger, Pirna (DE)

(73) Assignee: GeSIM Gesellschaft Fur Silizium-Mikrosysteme mbH Rossendorfer Technologiezentrum, Grosserkmannsorf (DE)

( * ) Notice: Subject to any disclaimer, the term of this patent is extended or adjusted under 35 U.S.C. 154(b) by 501 days.

(21) Appl. No.: 10/868,085

(22) Filed: Jun. 15, 2004

(65) Prior Publication Data

US 2004/0253821 A1 Dec. 16, 2004

(30) Foreign Application Priority Data

Jun. 16, 2003 (DE) .................... 203 09 374 U (51) Int. Cl.
*B21D 53/76* (2006.01)
*B23G 17/00* (2006.01)

(52) U.S. Cl. ............... 29/890.1; 29/592.1; 29/890.53; 156/349; 156/358; 156/359; 204/409; 204/412; 204/415; 422/68.1; 422/80.01; 422/100; 422/211; 435/288.5; 438/689

(58) Field of Classification Search ............... 29/592.1, 29/890.1, 890.53; 156/349, 358, 359; 204/409, 204/412, 415, 451–455; 422/68.1, 80.01, 422/100–104, 211; 435/288.5; 438/689

See application file for complete search history.

(56) References Cited

U.S. PATENT DOCUMENTS 5,520,787 A * 5/1996 Hanagan et al. ....... 204/403.14
6,557,582 B2 * 5/2003 Krog ..................... 137/599.03
7,114,541 B2 * 10/2006 Howitz et al. ............. 156/349

FOREIGN PATENT DOCUMENTS

WO WO 02/21115 A1 3/2001

OTHER PUBLICATIONS

"Fabrication and evaluation of amperometric sensors for micro flow cell using 3-D comb electrodes"; Honda, N.; Emi, K.; Katagiri, T.; Kawakami, S.; Irita, T.; Shoji, S.; Sato, H.; Homma, T.; Osaka, T.; Microprocesses and Nanotechnology Conference, 2002; Nov. 6-8, 2002; pp. 290-291.*
Warner Instruments—A Harvard Apparatus Company, "Specialized Tools for Electrophysiology & Cell Biology Research", 2002 Product Catalog, S. 172).
Ippei Inoue, et al., "On-Chip Culture System for Observation of Isolated Individual Cells", Lab on a Chip, 2001, 1(1), 50-55.

* cited by examiner

Primary Examiner—Paul D. Kim
(74) Attorney, Agent, or Firm—Baker Botts L.L.P.

(57) ABSTRACT

The invention relates to a method of producing a 3-D microscope flow-through cell, consisting of an upper and a lower substrate between which is located a flow channel, an electrode structure penetrating the flow channel and connected with external contacts and with through-connections at the ends of the flow channel for the connection of fluid inlets and outlets. The invention provides a method of producing 3-D microscope micro flow-through cells that are suitable for the reversible assembly of microscope flow-through cells for the μm-volume range. According to the invention, this is obtained in that a base substrate is first provided with access holes and a flow channel, the flow channel being made of a sandwich of a material non-elastic inside and elastic outside, in that the flow channel for the purpose of a fluid-tight channel closure, is pressed against a second cover glass in order to provide a reversibly sealable flow channel.

11 Claims, 6 Drawing Sheets

METHOD FOR PRODUCING A 3-D MICROSCOPE FLOW-THROUGH CELL

FIELD OF THE INVENTION

Then present invention relates generally to a method of producing a 3-D microscope flow-through cell, and more particularly to a flow through cell having an upper and a lower substrate between which is located a flow channel, an electrode structure penetrating the flow channel and connected with external contacts and with through-connections at the ends of the flow channel for the connection of fluid inlets and outlets.

BACKGROUND OF THE INVENTION

Microscope slide assemblies having a fluid flow-through cell are generally known in the art. For example, the Warner Instruments firm offers microscope chambers for the ml-volume range for micro incubation, for cell microscopy and for cell perfusion. As one of the first manufacturers of such microscope accessories, Warner Instruments has taken on the subject of reversibly assemblable micro flow-through cells. (As used herein, the term reversibly assemblable refers to a product which can be assembled. The principle of the closed microscope chamber can best be seen in the design of flow-through cells for confocal cell microscopy (cf. Warner Instruments Catalog 2002, p. 172). A flat silicon seal in the range of 250 to 1000 µm thick is placed between two cover glasses which are approximately 150 µm thick. One of the cover glasses has openings for the access of fluid. This threefold connection is inserted into a two-piece concentric support and is pressed into a fluid-tight relationship by screwing the two supports into each other. The upper cover plate of the concentric support, for which there is room on the microscope work plate, contains the fluid inlets.

This method permits the use of at least one disposable cover glass and of a second, apertured cover glass or a slide, especially adapted to the design of the flow-through channel. The channel geometry is limited to that which is technically feasible in the structuring of the flat silicon seal, i.e., the channels are only accurate to one millimeter and can be made no thinner than 250 µm. A further drawback is that the channels can only have rough contours and cannot be fabricated with internal channel barriers, such as flow guides or flow splitters. Further, the channels cannot be adjusted accurate to microns to structures of one or both cover glasses, and numerous applications with electrically functionalized surfaces simply cannot be performed.

The flat silicon seal is relatively costly, has a complicated chamber assembly that can easily be maladjusted in installation and is hard to keep clean. Owing to the restrictions in geometry, only relatively large-volume channels can be realized, and therefore Warner Instruments only offers the system for the ml-volume range.

The firm of Ibidi GmbH offers a new generation of µ-slides, which are suitable as microscope supports of synthetic material for common and high-resolution microscopy methods, such as for example DIC, phase contrast, fluorescence and transmitted light. This slide-based technique is directed to use as a disposable product on the microscope, designed to work without connection to components of automated external fluidics.

Another product known in the art is the so-called µ-slide I, which is offered as a flow-chamber system for cell culture and in vitro cell microscopy. This system is an irreversibly connected channel system, consisting of two planes of synthetic material—the embossed base and a perforated cover. The µ-slide I consists of a 100-µl channel, which on both sides ends in a 2-ml fluid reservoir. The 2-ml reservoirs in practice form a cell culture dish which is directly connected to the simple flow-through system for microscopic observation of appropriate objects on the inverse microscope. Objects are flowed into the channel, and flow parameters and fluid composition are not influenced, as is possible with the connection of external pumps and valves.

A second product defining the related art is Ibidi GmbH's µ-slide V. Designed according to the principle of the µ-slide I, this is also a flow-chamber system for simultaneous protein analysis in five channels running parallel through the microscope image field and each holding 17 µl. The fluid connections to the five channels each form an inlet and outlet reservoir and, here again, there is no possibility of influencing flow parameters by external fluidics.

A third product defining the known art is the micro array µ-slide of Ibidi GmbH. This is a two-piece flow-chamber system, still open before use for work on the microscope, consisting of two parts of synthetic material, the embossed base and the one-time self-adhesive unembossed cover.

The µ-slide is primarily used for rapid micro array analysis by in-situ hybridization in a flow-through mode. For this purpose, the micro array is produced by using a spotting technique in the chamber region of the initially open base, then the cover is irreversibly applied and flow-through hybridization can take place.

After hybridization of the array, evaluation under the microscope takes place and then the slide is discarded. The fluid circuit is characterized by an inlet opening for conventional disposable plastic pipette tips, the 10 to 400 µl-reaction chamber and a collecting reservoir at the outlet of the reaction chamber.

Corresponding to its principle of use as a disposable diagnostic system, Ibidi microscope cells are low-cost disposable items and, as such, are suitable for a very limited area of application in terms of method. Flow-through analyses, test procedures or handling techniques that require continuous flow-through operation cannot be performed with the Ibidi systems µ-slide.

Several firms have recently offered flow-through cells for microscopy in the µl-volume range; these systems are based on glass, ceramic, synthetic material or silicon and permit inclusion of the growing field of microsystem technology, biotechnology and nanotechnology.

Ippei Inoue has developed a cell culture system on chips—the glass array slide used as a micro flow-through cell for work under the optical microscope [Ippei, Inoue, et al.; On chip culture system for observation of isolated individual cells; Lab on a Chip, 2001 1, 50-55]. The system was a glass slide in which microcavities arranged array-like are etched. The micro flow-through cell is produced by application of a covering plate on the array slide. If this micro flow-through cell is placed on the work plate of an inverse microscope and connected to an external fluid supply, the fluidic process and microscopic observation can be performed simultaneously.

The microcavities are produced by isotropic etching of the glass. The microcavities introduced measure in the range of 20 to 70 µm in diameter and about 5 to 30 µm in depth. After etching, the surface of the glass was functionalized on a nano scale by attachment of amino groups and biotin. Commercially available chemicals, which were applied to the glass by immersion, tempering and wash techniques can be used for this purpose. The microcavities are then filled with cells and sealed with a semi-permeable cellulose membrane functionalized with streptavidin. Thus, in this system, the biotin-streptavidin connection provides a reliable sealing mechanism between the microcavities filled with cells and the membrane. Accordingly, this closure is effected without cementing and without elastic sealing.

This is an example of the use of strong biotin-streptavidin bonding for solving an assembly problem in biotechnology. If this cell-based array slide is produced on the slide, a micro scale single-channel glass cover is placed on top and nutrient solution can be supplied from outside. The replacement of nutrient medium in each micro cavity covered with a cellulose membrane takes place by diffusion through the covering membrane. The disadvantage of this biotechnological assembly method is that a biochemically realizable biotin/avidin contact is permanently connected.

Another example of the realization of microscope cells is a method proposed by the GeSiM firm in patent PCT/DE 01/03324. Here, photolithographic structuring techniques and SMD assembly technology are linked in such a way that base glass and cover glass of the microscope cell may be positioned to one another accurate to microns, and permanently cemented together. This technology is very interesting for reusable products, but clearly too costly for disposable products.

OBJECTS AND SUMMARY OF THE INVENTION

The object of the invention is to provide a method of producing 3-D microscope micro flow-through cells that are suitable for the reversible assembly of microscope flow-through cells for the µl-volume range, which are open for utilization of modern microtechnologies and permit inexpensive utilization of disposable microscopy items.

The combined use of microsystem technology, such as glass drilling (e.g.: US drilling or micro sandblasting), photolithographic polymer structuring (e.g.: photosensitive resists or photoepoxy resins) and such as silk-screen printing of elastic sealing layers (e.g., silicon rubber, PDMS), permits a slide for microscopy to be functionalized so that a reversibly assemblable micro flow-through cell for the µl-volume range can be produced. According to the invention, microscope flow-through cells constructed in this way are easy to remove after use, the used cover glass can be discarded and after cleaning the functionalized slide can be used over again.

In use, the slide and the cover glass (e.g., 150 -µm disposable cover glass) form a micro flow-through cell in that both parts are placed in a mechanical frame, a so-called support, and exactly adjusted to one another. The support in turn is adjusted in the optical path of the rays of the microscope in such a way that the microscope cell is brought exactly into the plane of observation of the microscope. In addition, the support is constructed in such a way that the two joining parts, the slide and the cover class, are pressed together in a fluid-tight relationship.

The seal, which is required for fluid-tight sealing of the two substrates, is applied to the slide prior to assembly to the support in such a way that it can be used repeatedly and can easily be cleaned between the replacement processes of the cover glasses.

Owing to the construction of the support, which is adapted to the size of the two glass substrates, this connection is effected without expenditure of significant mechanical effort. The connection can be made virtually blindly and is adjusted only over the outside dimensions of the joining partners. The low dead-volume fluid connection of the microscope flow-through cell with external fluidic components such as pumps, valves, mixers and sensors is ensured by O-rings pressed directly onto the slide.

The emphasis of the invention is on the technical realization of the system of the micro channel and sealing system in a structural union, i.e., the seal and micro channel are produced as a multilayer connection and by application of a special technological manufacturing routine. This manufacturing routine comprises the planar technologies of the micro system technique, such as photolithography and silk-screen printing.

Applications for this device are extensive as a result of the fact that the disposable product, the cover glass, can be brought directly into engagement with the reusable product, the slide. However, a prerequisite is that the reusable product be specifically pretreated. In this way, the user may serially test as many disposable products as desired, pretreated in various ways, in a microfluidic channel system as demanding as desired.

The present invention lends itself to many possible applications, such as: fluorescence microscopy, fluorescence in-situ hybridization (FISH), confocal microscopy, combination of laser desection and sample re-treatment or sample storage, DNA handling and DNA hybridization in flow-through, capillary electrophoresis and dielectrophoresis, reaction kinetics, cell stress in simultaneous thermal shock, in change of ion concentration, mobility assays as a form of cell vitality test under specific fluid conditions and micro assembly of functionalized cover glass surfaces in nanotechnology.

BRIEF DESCRIPTION OF THE DRAWINGS

The invention is now to be described in detail by an exemplary embodiment. In the accompanying drawings.

DETAILED DESCRIPTION OF THE PREFERRED EMBODIMENTS

Figure 1A:
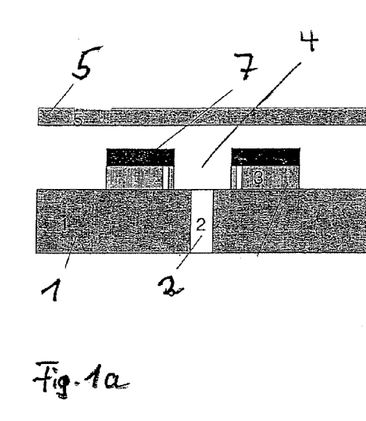
FIG. 1a is a simplified cross-sectional view showing the sealing principle in a 3-D microscope micro flow-through cell according to the invention, consisting of a glass slide and a cover glass, before assembly.
Figure 1B:
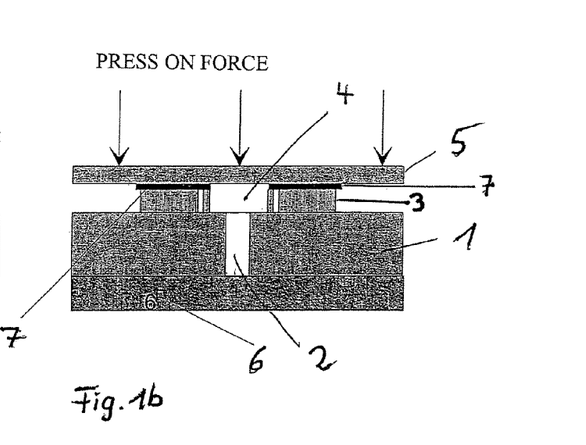
FIG. 1b is a simplified cross-sectional view showing the sealing principle in a 3-D microscope micro flow-through cell according to the invention, consisting of a glass slide and a cover glass, after assembly.

The basic element of the device according to the invention, shown in FIGS. 1a and 1b, consists of the slide 1 disposed on support 6, and the cover glass 5. The slide 1 has access holes 2 and the channel system 4. The diameter of the access holes is in the range of 200 to 1000 µm, and the thickness of the glass slide is about 0.5 to 1.5 mm. The arrangement of the holes may be specified by the particular application, but it may alternatively be designed in the form of a universal apertured plate in such a way that a number of different applications can be satisfied with a single slide configuration. The channel and sealing system found on the inside of the slide, a connection made of a hard core material 3 and an elastic sealing material is fabricated microtechnologically. The design is governed by the individual channel shape suggested by the particular application.

The channel systems may be made with unlike dimensions and materials for the core and seal. The width and height of the hard core material 3 for the channel may be between 5 µm and several 100 µm. The hard core material 3 of the channel system may be obtained by structuring of a photopolymer, by etching of the glass slide or by etching of silicon.

For the purpose of sealing, the surface of the hard core material 3 is coated with an elastic, strongly adhesive polymer. For this, preferably silicon rubber 7 is applied by silk-screen printing or stamp printing. The height of the channel system composed of hard core material 3 and silicon rubber 7 is governed principally by the thickness of the hard core material, typical values being 5 to several 100 µm. The channel width may be selected from between several µm and several mm.

At this point, the channel system 4, formed on the slide 1 is a channel system which is still open at the top, as is only closed by connection with a second substrate, preferably a glass cover glass 5 only about 150 to 200 µm thick, s.

Figure 2A:
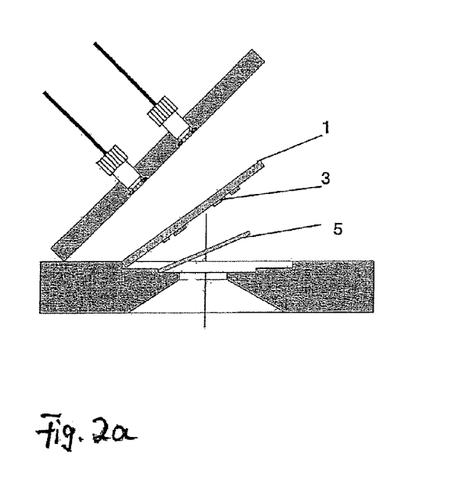
FIG. 2a is a simplified cross-sectional view showing a basic representation of a 3-D microscope micro flow-through cell as an installation sequence.
Figure 2B:
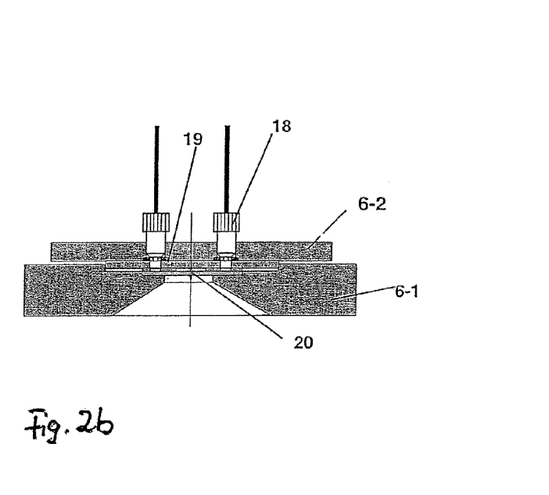
FIG. 2b is a simplified cross-sectional view showing a basic representation of a 3-D microscope micro flow-through cell in the assembled state.

The connection of slide 1 and cover glass 5 is effected in the so-called support, which consists of the lower support 6-1 and the upper support 6-2. The lower support 6-1 and upper support 6-2 can be pressed together by a spring force and guide pins such that the slide and the cover glass are joined together, thereby sealing off the fluid lying between these support plates. Production of the fluid-tight channel requires only minimal and relatively imprecise adjusting work, and formation of this connection, represented in FIG. 2, may be repeated as often as desired.

Since inexpensive and commercially available cover glasses 5 can be used for construction of the microscope cell, minimal limits are placed on the number of flow-through cells that can be realized. The cover glasses 5 may be functionalized chemically, biologically or physically before installation, depending upon the method. When functionalization has been completed, the cover glass can be joined to the slide within seconds and without extensive adjusting work to make a closed channel system.

Description of Special Exemplary Embodiments:

Depending upon the complexity of the micro channel system, the microfluidic, optical, chemical, physical and sensor demands, the specific construction of the microscope cell and the periphery can turn out differently. This is to be described further in the following exemplary embodiments.

EXAMPLE (A)

A Slide of Glass with Channel Systems Having Few Branches

Figure 4:
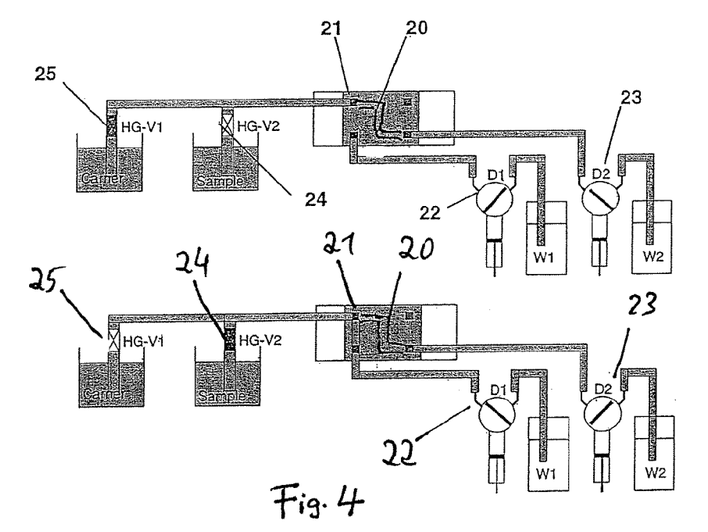
FIG. 4 is a schematic diagram of a fluidic system diagram with the sequences of filling and sample aspiration.

FIGS. 2 and 4 show microscope cells that are each composed of a glass slide 1 with standard dimensions of 75 mm×25 mm×1 mm and a cover glass 5 having dimensions of 22 mm×22 mm×0.15 mm. The slide has four (4) through-holes, i.e., the number of fluid connections available for channel systems in the example is limited to 4. Each of the four fluid connections 18 is provided with a sealing 19 and has a space requirement of 7.5 mm diameter and is in lateral alignment on the cover glass do not seriously interfere with optical transparency in the region of the flow channel 20.

Three fluid connections are used in the exemplary embodiment, two for the T-shaped entry channel and one for the outlet connection. A fluid connection is redundantly present in the exemplary embodiment.

As represented in the general description, the channel system is found on the glass slides. It consists of a 50 µm-high hard core material 3 of photopolymer and a 20 µm-thick silicon rubber seal 7, the connection being made in the two-piece support 6-1 and 6-2 to form a fluid-tight flow channel. In the inlet region of the flow channel 20, the channel system has a T-shaped channel intersection 21. This T-shaped channel permits low dead-volume sample injection into the observation channel 20. In an exemplary implementation, the height of the resulting flow channel can be determined from the polymer height according to the formula X * polymer height=resulting channel height, where X is in the range of about 1.30 to 1.45.

Figure 5:
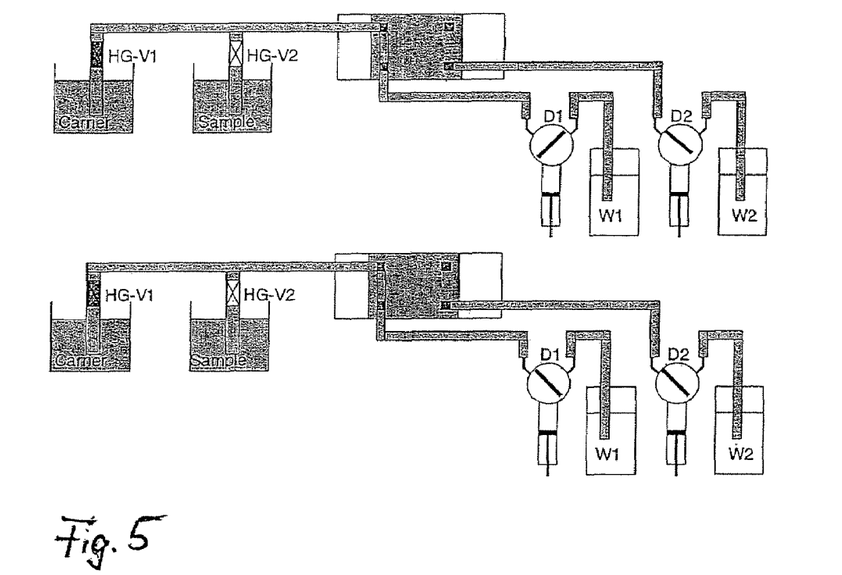
FIG. 5 is a schematic diagram of a fluidic system diagram with the sequences of sample injection and channel flushing.

In order to understand the function of the T-shaped channel 21, let us consider the fluidic sequences in FIGS. 4 and 5, in which the fluidic processes in filling, sampling, sample injection and in flushing in the channel system of the microscope cell are described. There are two injector pumps 22, 23 and two valves 24, 25 in the periphery of the system. If the injector pump 22 is turned on, with sample valve 25 open and carrier valve 24 closed, and at the same time the inlet valve of the injector pump 23 remains closed, a sample can be drawn in at the T-shaped channel inlet 21 while fluid is fixed in the channel 20. At the same time, it is advantageous that during this fluidic activity no influence of the fluid found in an image field occurs, if diffusion phenomena at this location are not considered. At the same time, however, at the inlet of the observation channel 20 complete replacement of solution occurs at the T-shaped inlet 21. In the example, at the T-shaped channel inlet 21 location a switch is made from the carrier fluid to the sample fluid. Now, if the carrier valve 24 is opened again, while the sample valve 25 is closed, the injector pump 22 turned off and sealed against the T-shaped channel inlet 21, exact and low dead-volume sample injection into the flow channel 20 can be realized with the injector pump 23.

EXAMPLE (B)

Figure 7:
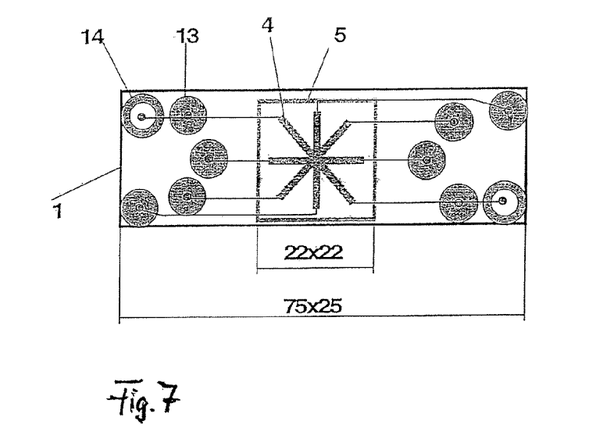
FIG. 7 is a top view of a microscope cell, consisting of manifold slide, cover glass and passive as well as active hose fittings.

Multilayer Slide of Glass-Silicon for Applications Having Highly Branched Channel Systems A multilayer slide with cover glass 5, which has eight fluid connections on a cover glass surface of 22×22 mm$^2$, is shown in FIG. 7. With reference to the principle of construction mentioned above with respect to Example (a), this object could not be accomplished for reasons of space, since the large number of hose connections, cannot be accommodated on the slide. One way to solve the problem would be to enlarge the cover glass enough for the fluid connections to have room in the edge region of the cover glass.

Figure 6:
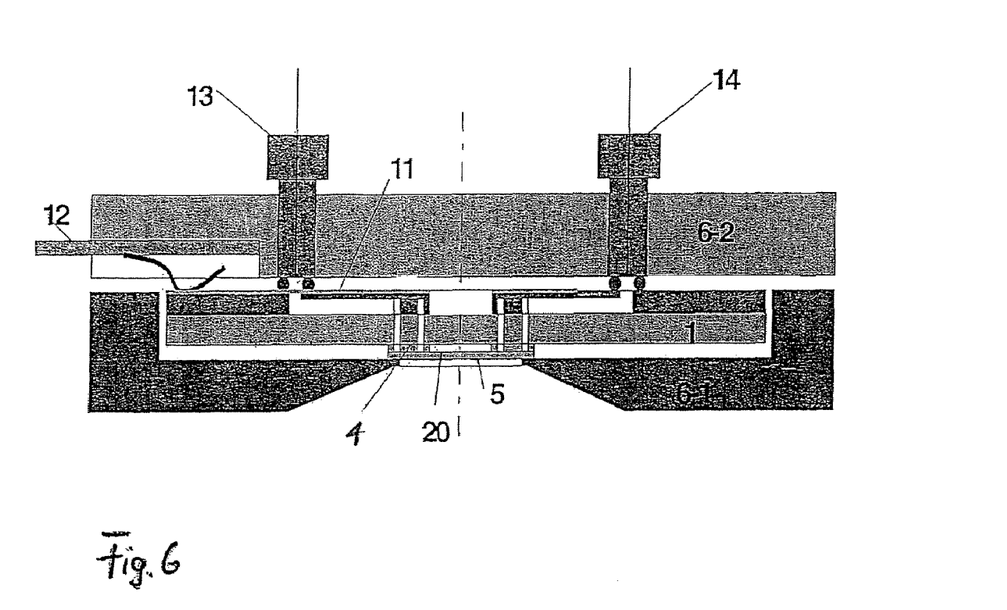
FIG. 6 is a simplified cross sectional view showing a microscope cell in the two-piece support, consisting of manifold slide with electrodes, cover glass and passive and active connection fittings.

The embodiment of the invention as illustrated in FIG. 6 does not start out from enlargement of the cover glass 5, but here a slide 1 is described, which has its manifold, apertured plate and channel support all in one. Because the channels located in the manifold of the slide mediate between the fluid connections located in the outer region of the slide and the fluid connections concentrated under the cover glass, a great many fluid connections can be concentrated on the cover glass and at the same time accommodate space-consuming hose connections in the outer region of the slide without interfering with optical function. According to the invention, the slide designed as a manifold is preferably constructed as a multi-layer system.

FIG. 6 shows a silicon-glass connection 1 with holes in the silicon and in the glass, dimensions of 75 mm×25 mm×1.4 mm and function metallization on the silicon back side 11. On the front side of the silicon-glass connection 1 is again found the flow channel 4, and 20, which has the star shape shown in FIG. 7, and, here too, sealing is effected by the supports 6-1 and 6-2 by pressing against the cover glass 5. Fluidic drive takes place as described above in connection with Example (a), with external fluidic structural groups.

EXAMPLE (C)

Microscope Cells with Active Hose Connections

A microscope cell which, in addition to passive hose connections 13, also has active hose connections 14, is shown in FIG. 7. The active hose connection 14 includes a micro-valve that is integrated directly into the flow channel of the fitting. Execution of the active fitting may be realized as a hose fitting as represented in FIG. 3a, or an injector fitting as shown in FIG. 3b.

Figure 3A:
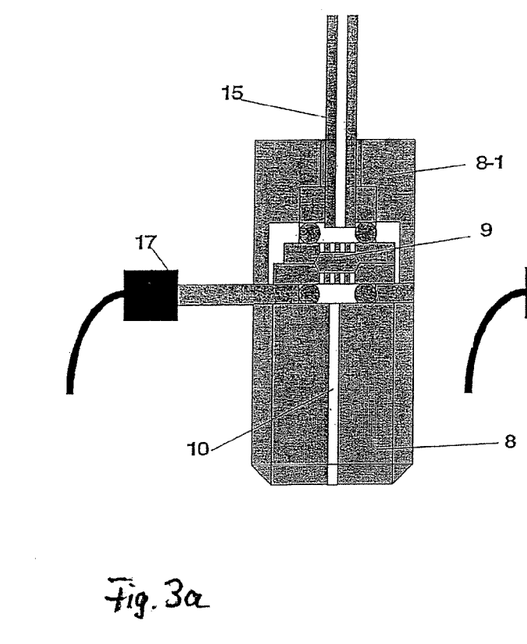
FIG. 3a is a simplified cross-sectional view showing actively switching fluidic connection fittings with a hydrogel micro valve with a hose fitting.

The hose fitting shown in FIG. 3a consists of a two-piece housing of synthetic material, the basic member 8 provided with an outlet 10, and the cover 8-1. These housing parts are preferably screwed together with a printed circuit board 17 after insertion of the micro-valve 9. A hose 15, running in from outside, is pressed fluid-tight against the silicon member of the micro valve 9 when the housing parts are screwed together. The micro-valve 9, designed in the exemplary embodiment as an opener valve with a hydrogel actuator, may be opened by the electrical connection 17 with a contact rating of about 200 mW. In the electrically idle state, the valve 9 remains closed and may be loaded leakage-free with a pressure of at most 6 bar.

Figure 3B:
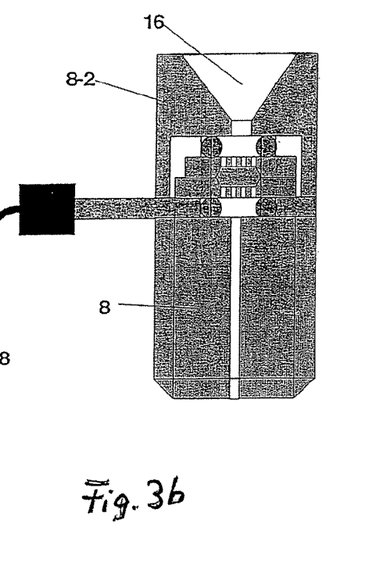
FIG. 3b is a simplified cross-sectional view showing actively switching fluidic connection fittings with a hydrogel micro valve with a manual injector fitting.

The injector fitting shown in FIG. 3b consists of a two-piece housing of synthetic material, the base member 8 and the cover 8-2. The cover 8-2 has a funnel opening 16, into which the sample may be pipetted manually or by automatic metering apparatus. These housing parts are screwed together with the printed circuit board 17 after insertion of the micro valve 9. If the opener valve is electrically opened by the hydrogel actuator, a defined volume of sample can be sucked into the microscope cell. An advantage of this embodiment is that there is no leakage in the direction of the microscope cell when the micro-valve in the injector fitting is disconnected.

Figure 8:
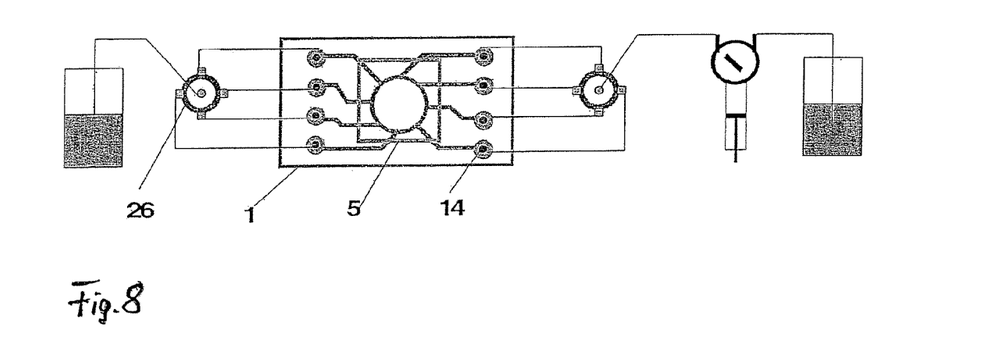
FIG. 8 is a schematic diagram of a system example of a microscope cell with manifold slide and active hose fittings.

Shown in FIG. 8 is a system layout of the microscope cell with active hose fittings, which permits the realization of a complex fluidic logic without the use of external macro valves.

Figure 9:
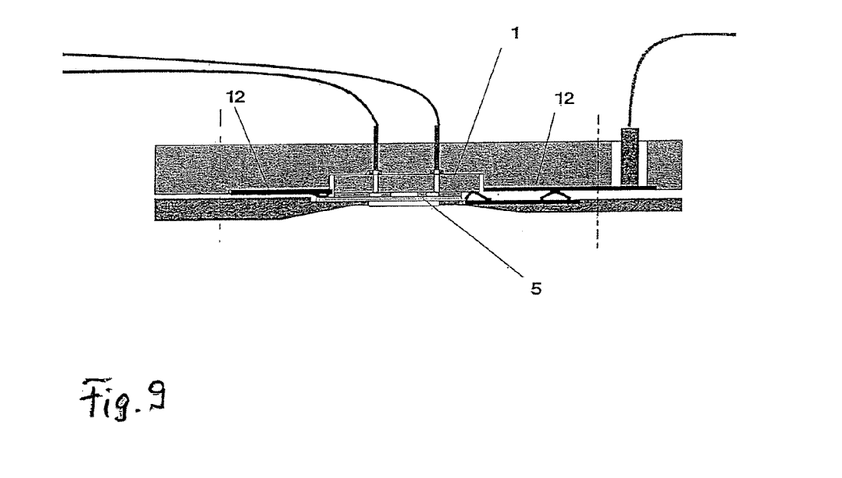
FIG. 9 is a simplified cross-sectional view showing a reversibly assemblable microscope cell for operation with slide and cover glass, which bear electrodes on both sides.

In addition, the reversibly assemblable microscope flow-through cell may be provided on the slide (drilled, channel-bearing, approximately 1 mm thick) as well as on the cover plate (thickness 150 μm) with electrodes, which are tapped by spring contact strips and connected to external electronics (FIG. 9).

EXAMPLE (D)

Polydimethylsiloxane (PDMS) Channel Plate

Figure 10:
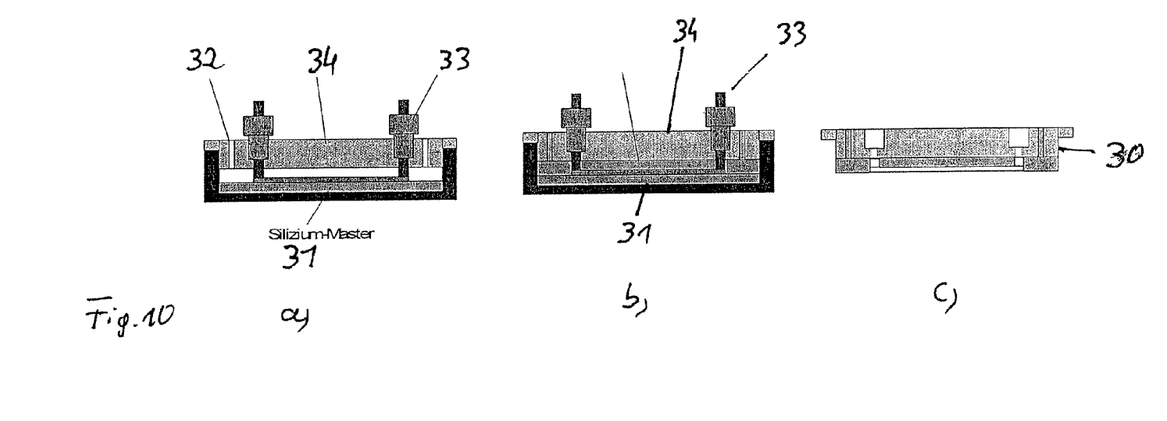
FIG. 10a is a cross-sectional view demonstrating the shaping process for production of a PDMS channel plate, with a shaping tool, before filling with PDMS.
FIG. 10b is a cross-sectional view of the PDMS channel plate and shaping tool after filling with PDMS.
FIG. 10c is a cross-sectional view of a finished PDMS channel plate.
Figure 11:
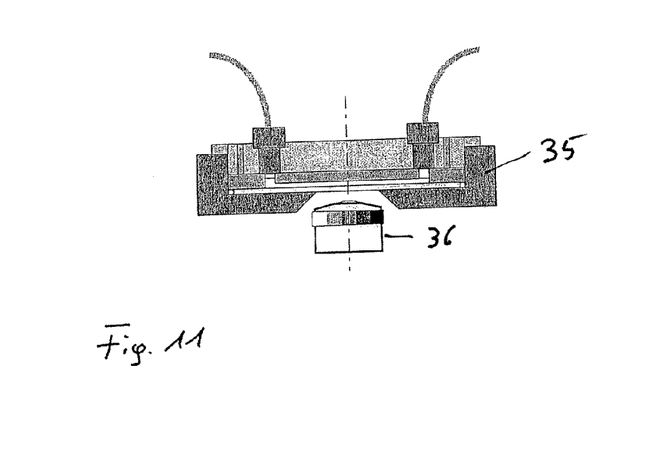
FIG. 11 is a cross-sectional view of a microscope cell with the PDMS channel plate of FIG. 10c.

The production of a PDMS channel plate 30 is represented in FIGS. 10 and 11. FIG. 10a shows the shaping process for production of the PDMS channel plate 30 with a shaping tool (silicon-negative structure 31) before filling with PDMS and FIG. 10b the shaping tool after filling with PDMS by a PDMS inlet 32 as well as channel stoppers 33 in a PMMA plate 34. Lastly, a finished PDMS channel plate 30 is represented in FIG. 10c.

FIG. 11 shows a ready-to-use microscope cell with the PDMS channel plate.

Channel systems with the PDMS channel plate 30 meet the highest demands for accuracy, since the shaped structures are produced by microfabrication technologies in silicon and shaping of the silicon master on the PDMS silicon rubber takes place almost error-free. In order to obtain good shaping properties, the silicon master can be plasma-chemically provided with a Teflon coating.

In this case, the channel, the seal to the cover glass and the fluid connection can be produced in one operation with the accuracy of photolithographic technology.

The microscope cell of FIG. 11 consists of a mechanical support 35 for accommodation of the PDMS channel plate 30 for adaptation to a microscope (microscope objective 36) or to another device, as well as the external fluidic components such as pumps, valves, sensors, mixers, etc.

EXAMPLE (E)

PDMS Channel Plate with Fiber Connector

Figure 12:
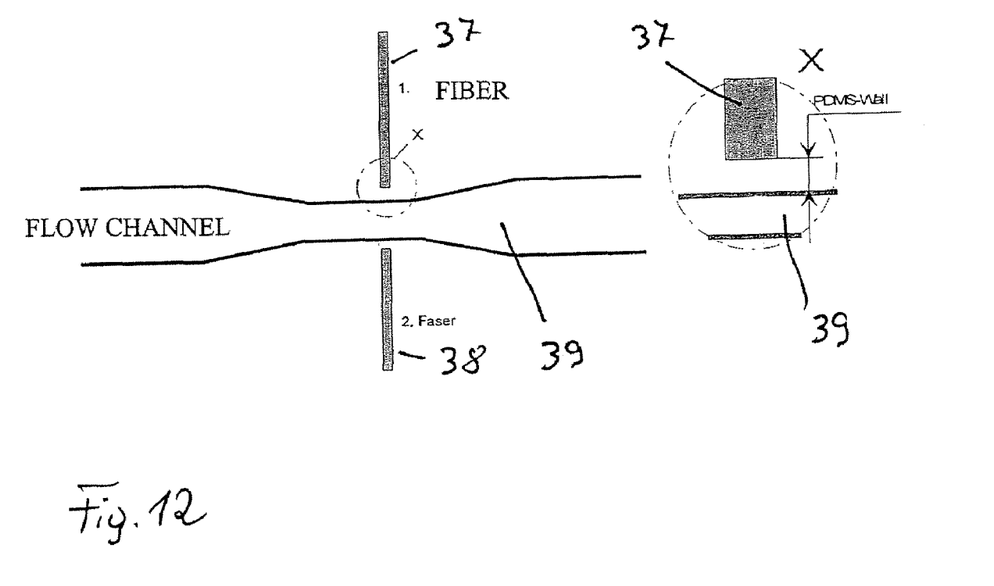
FIG. 12 is a cross-sectional view of an example of a fiber connector on the PDMS channel plate.

FIG. 12 shows the principle of a fiber connector on the PDMS channel plate. In order to apply a fiber connector from fibers 37, 38 to the PDMS plate 30, the flow-through channel 39, as well as a cavity for the guidance of one or more optical fibers 37, 38 are produced in the shaping process of the silicon master (silicon-negative structure 31).

Here, fixation of the optical fibers 37, 38 is effected in the elastic silicon rubber, while a thin residual skin of at least 10 μm remains preferably between the fluid-conducting channel 39 and the optical fibers 37, 38, thereby permitting fluid-tight connection of the fibers 37, 38 without any problem.

Selection of a sufficiently long guide length of the optical fibers in the PDMS permits arrangement of the fibers 37, 38 which is accurate to one µm with reference to the flow-through channel 39. The elastic bulk material, i.e., the PDMS, will not generally damage the fibers 37, 38 mechanically. Owing to the relatively great hardness of the PDMS, a reversibly assembled arrangement of the optical fibers 37, 38 is provided. When an optical coupling oil is used, a substantially perfect index contact can be obtained.

What is claimed is:

1. A method of producing a 3-D microscope flow-through cell, the cell having an upper and a lower substrate confining a flow channel, an electrode structure penetrating the flow channel and connected with external contacts, and through-connections to the ends of the flow channel for the connection of fluid inlets and outlets, the method comprising:

disposing an uncovered flow channel on the lower substrate, wherein the uncovered flow channel is defined by a bi-layer structure comprising a bottom layer of non-elastic material and a top layer of elastic material;

disposing the substrates in a pressing support structure so that the upper substrate is pressed on the elastic material to cover and reversibly seal the flow channel fluid tight.

2. The method according to claim 1, wherein disposing an uncovered flow channel on the lower substrate comprises photolithographically patterning polymer material and hardening the polymer material to form the layer of non-elastic material.

3. The method according to claim 2, wherein disposing an uncovered flow channel on the lower substrate comprises disposing an uncovered flow channel on the lower substrate so that the height of the resulting flow channel is about 1.30 to 1.45 times the polymer height.

4. The method according to claim 1, wherein disposing an uncovered flow channel on the lower substrate comprises disposing an elastomer material to form the layer of elastic material.

5. The method according to claim 1, wherein disposing an uncovered flow channel on the lower substrate comprises silk-screen printing the elastic material.

6. The method according to claim 1, wherein the upper substrate is a cover glass, and wherein disposing an uncovered flow channel on the lower substrate comprises disposing the uncovered the low channel on an upper side of the lower substrate.

7. The method according to claim 6, wherein disposing an uncovered flow channel on the lower substrate comprises disposing fluid inlets and outlets in the lower substrate that are branched in a three-dimensional arrangement.

8. The method according to claim 1, wherein disposing an uncovered flow channel on the lower substrate comprises integrating micro valves in the lower substrate.

9. The method according to claim 1 further comprising attaching a micro valve to the lower substrate with a screw.

10. The method according to claim 1, wherein disposing an uncovered flow channel on the lower substrate comprises forming a three-dimensional channel system by pouring PDMS (polydimethylsiloxane) on a plate.

11. The method according to claim 10, wherein the plate comprises silicon and wherein forming the three-dimensional channel system comprises shaping the three-dimensional channel system with shaping structures formed in silicon.

* * * * *